(12) United States Patent
Baarstad et al.

(10) Patent No.: US 9,470,662 B2
(45) Date of Patent: Oct. 18, 2016

(54) SENSOR MODULE WITH ADAPTIVE BACKING LAYER

(71) Applicant: DolphiTech AS, Raufoss (NO)

(72) Inventors: Tore Baarstad, Lillehammer (NO);
Eskil Skoglund, Gjøvik (NO);
Arnt-Børre Salberg, Hamar (NO);
Johan Skjelstad, Elverum (NO)

(73) Assignee: DolphiTech AS (NO)

( * ) Notice: Subject to any disclaimer, the term of this patent is extended or adjusted under 35 U.S.C. 154(b) by 206 days.

(21) Appl. No.: 14/071,253

(22) Filed: Nov. 4, 2013

(65) Prior Publication Data

US 2015/0053013 A1    Feb. 26, 2015

(30) Foreign Application Priority Data

Aug. 23, 2013   (GB) .................................. 1315090.9

(51) Int. Cl.
| G01N 29/26 | (2006.01) |
| G01N 29/04 | (2006.01) |
| G01N 29/22 | (2006.01) |
| G01N 29/28 | (2006.01) |

(52) U.S. Cl.
CPC ............ G01N 29/26 (2013.01); G01N 29/043 (2013.01); G01N 29/226 (2013.01); G01N 29/28 (2013.01); G01N 2291/044 (2013.01); G01N 2291/102 (2013.01); Y10T 29/49826 (2015.01)

(58) Field of Classification Search
None
See application file for complete search history.

(56) References Cited

U.S. PATENT DOCUMENTS

| 3,778,756 A | 12/1973 | Houston |
| 3,895,525 A | 7/1975 | Eichelberger et al. |
| 4,441,369 A | 4/1984 | Lessard et al. |
| 5,383,366 A | 1/1995 | Wallingford et al. |
| 5,773,811 A | 6/1998 | Schramm, Jr. et al. |
| 6,748,259 B1 | 6/2004 | Benaron |
| 7,675,045 B1 | 3/2010 | Werner |
| 8,453,928 B2 | 6/2013 | Melandsø et al. |
| 2002/0062083 A1 | 5/2002 | Ohara et al. |
| 2003/0145655 A1 | 8/2003 | Lorraine et al. |
| 2005/0279171 A1 | 12/2005 | Kollgaard |
| 2006/0219013 A1 | 10/2006 | Baba et al. |
| 2007/0084290 A1* | 4/2007 | Fetzer ................ G01N 29/0645 73/627 |
| 2008/0000299 A1 | 1/2008 | Georgeson |
| 2008/0208061 A1 | 8/2008 | Halmann |

(Continued)

FOREIGN PATENT DOCUMENTS

| CN | 102680583 | 9/2012 |
| DE | 202131052252 | 4/2014 |

(Continued)

OTHER PUBLICATIONS

UK Intellectual Property Office, Search Report, Application No. GB1413618.8, Jan. 27, 2015, 2 pages.

(Continued)

*Primary Examiner* — Robert R Raevis
(74) *Attorney, Agent, or Firm* — Fish & Richardson P.C.

(57) ABSTRACT

A scanning apparatus comprising a receiver circuit and a transmitter circuit, both circuits being flexible such that they are capable of conforming to the surface contours of an object as a surface of the apparatus is pressed against it and an adaptive backing positioned behind the transmitter and receiver circuits in the scanning apparatus and configured to, as the scanning apparatus is pressed against the object, conform to the flexible circuits.

18 Claims, 4 Drawing Sheets

(56) References Cited

U.S. PATENT DOCUMENTS

| | | | |
|---|---|---|---|
| 2009/0082673 A1* | 3/2009 | Lu | A61B 8/4281 600/459 |
| 2010/0274139 A1 | 10/2010 | Fukukita et al. | |
| 2011/0040187 A1* | 2/2011 | Matsumura | A61B 5/6843 600/443 |
| 2012/0192651 A1 | 8/2012 | Lee et al. | |
| 2013/0030727 A1* | 1/2013 | Zalameda | G01N 29/045 702/56 |

FOREIGN PATENT DOCUMENTS

| | | |
|---|---|---|
| EP | 1621135 | 11/2006 |
| EP | 2249152 | 11/2010 |
| GB | 2109555 * | 6/1983 |
| GB | 2286678 | 8/1995 |
| GB | 2432671 * | 5/2007 |
| JP | 60-102553 | 6/1985 |
| JP | 60-102554 | 6/1985 |
| JP | 08-075714 | 3/1996 |
| JP | 2010060520 A | 3/2010 |
| WO | WO2008/137030 | 11/2008 |
| WO | WO2011/089537 | 7/2011 |
| WO | WO2013/161834 | 10/2013 |

OTHER PUBLICATIONS

UK Intellectual Property Office, Search Report, Application No. GB1413616.2, Jan. 28, 2015, 2 pages.

UK Intellectual Property Office, Search Report, Application No. GB1315090.9, Jan. 30, 2015, 2 pages.

Cincotti et al.: "Efficient transmit beamforming in pulse-echo ultrasonic imaging", IEEE Transactions on Ultrasonics, Ferroelectrics and Frequency Control, IEEE, US, vol. 46, No. 6, Nov. 1, 1999, pp. 1450-1458, XP011438016.

Endrerud, Jan Olav; Skoglund, Eskil: "DolphiCam User Manual", Jun. 27, 2013, XP055179749, Raufoss, Noway, http://www.dolphitech.com/wp-content/uploads/2014/12/DolphiCam-User-Manual-1.1-27.06.2013.pdf.

European Extended Search Report issued in EP application No. 14185307.7 dated Apr. 20, 2015, 7 pages.

Gustafsson, M. G., et al., "Split Spectrum Algorithms Rely on Instantaneous Phase Information—A Geometrical Approach," IEEE Transactions on Ultrasonics, Ferroelectrics, and Frequency Control, vol. 40, No. 6, Nov. 1993, pp. 659-665.

Niblack, Wayne, "Digital Image Processing," 1986 Prentice-Hall International, 217 pages.

Persson et al.: "Electric excitation of ultrasound transducers for short pulse generation", Ultrasound in Medicine and Bioligy, New York, NY, US, vol. 7, No. 3, Jan. 1, 1981, pp. 285-289, 291, XP026374039.

Rubbers, Philippe, et al., "An Overview of Split Spectrum Processing," NDT.net Aug. 2003, vol. 8, No. 8, http://www.ndt.net/article/v08n08/rubbers.htm, 10 pages.

Stoica, Petre, et al., "Transmit Codes and Receive Filters for Radar," IEEE Signal Processing Magazine, Nov. 2008, pp. 94-109.

Tian, Qi, et al., "Multiple Target Detection Using Split Spectrum Processing and Group Delay Moving Entropy," IEEE Transactions on Ultrasonics, Ferroelectrics, and Frequency Control, vol. 42, No. 6, Nov. 1995, pp. 1076-1086.

Tomasi, C., et al., "Bilateral Filtering for Gray and Color Images," Proceedings of the 1998 IEEE International Conference on Computer Vision, Bombay, India, 8 pages.

Data Presentation. (Jun. 25, 2003). Retrieved Jan. 19, 2016, from http://www.nde-ed.org/EducationResources/CommunityCollege/Ultrasonics/EquipmentTrans/DataPres.htm.

Olympus NDT. EPOCH 1000 Series User's Manual. 910-269-EN—Revision B Jun. 2011.

Ultrasound and Ultrasonic Testing. (May 19, 2003). Retrieved Jan. 19, 2016, from http://www.nde-ed.org/EducationResources/HighSchool/Sound/ubraso1.nc1.htm.

[online] 1 Introduction to DolphiCam, Published on Aug. 7, 2013 by DolphiTech, to be accessed online at <https://www.youtube.com/watch?v=uPZnT78L_PE> Feb. 16, 2016.

[online] 2 Unboxing, Published on Aug. 7, 2013 by DolphiTech, to be accessed online at <https://www.youtube.com/watch?v=wcvStX941B0> Feb. 16, 2016.

[online] 3 The Camera, Published on Aug. 7, 2013, by DolphiTech, to be accessed online at <http://www.youtube.com/watch?v=-G9aJkBdegM> Feb. 16, 2016.

[online] 4 Getting Started, Published on Aug. 7, 2013 by DolphiTech, to be accessed online at <https://www.youtube.com/watch?v=x_hhrKvGPgk> Feb. 16, 2016.

[online] 5 Calibrating and Scanning, Published on Aug. 7, 2013 by DolphiTech, to be accessed online at <https://www.youtube.com/watch?v=jNNrN5C-Gz4> Feb. 16, 2016.

[online] 6 Scanning Boreholes, Published on Aug. 7, 2013 by DolphiTech, to be accessed online at < https://www.youtube.com/watch?v=FUd0SGe9UDg> Feb. 16, 2016.

[online] 7 Scanning Impact Damages, Published on Aug. 7, 2013 by DolphiTech, to be accessed online at < https://www.youtube.com/watch?v=il2bDgwL4Yg> Feb. 16, 2016.

[online] 8 3D Visualization, Published on Aug. 7, 2013 by DolphiTech, to be accessed online at <https://www.youtube.com/watch?v=TGcKxyAq_p0> Feb. 16, 2016.

[online] 9 Caring for the Camera, Published on Aug. 7, 2013 by DolphiTech, to be accessed online at < https://www.youtube.com/watch?v=LdgmJX9SS0E> Feb. 16, 2016.

* cited by examiner

SENSOR MODULE WITH ADAPTIVE BACKING LAYER

CROSS-REFERENCE TO RELATED APPLICATIONS

This application claims priority to United Kingdom Patent Application No. 1315090.9 entitled Sensor Module with Adaptive Backing Layer, which was filed on Aug. 23, 2013. The disclosure of the foregoing application is incorporated herein by reference in its entirety.

BACKGROUND

This invention relates to a scanning apparatus configured to transmit scanning pulses at a sample and receive reflections of those pulses from the sample.

Ultrasound is an oscillating sound pressure wave that can be used to detect objects and measure distances. A transmitted sound wave is reflected and refracted as it encounters materials with different acoustic impedance properties. If these reflections and refractions are detected and analysed, the resulting data can be used to generate images of the environment through which the sound wave traveled.

Ultrasound can also be used to scan a physical object. Most ultrasound frequencies are attenuated strongly by air and air-object boundaries tend to show a big impedance mismatch. Some form of coupling medium is needed if the ultrasound signals are to penetrate the object sufficiently. Often the coupling medium is a liquid, such as water or some form of gel.

Ultrasound can be used to identify particular structural features in an object. For example, ultrasound may be used for non-destructive testing by detecting the size and position of flaws in a sample. Non-destructive testing is typically performed in an industrial environment in which it is not practical to use a liquid coupling medium. U.S. Pat. No. 5,773,811 describes scanner that can be used for identifying material flaws in the course of non-destructive inspection procedures. It uses a gel pack to couple ultrasound energy into the substrate. This is more practical than using an uncontained gel but it can be difficult to accurately determine the depth of features below the substrate's surface. Dry couplings are also available, such as in the matrix code reading system of U.S. Pat. No. 8,453,928. Sample surfaces tend to be fairly flat in matrix-code reading applications, however, whereas surfaces are often uneven in non-destructive testing applications. Non-destructive testing applications also require the scanner to scan to greater depths than matrix-code reading applications.

SUMMARY

There is a need for an improved scanning apparatus.

According to one embodiment, there is provided a scanning apparatus comprising a receiver circuit and a transmitter circuit, both circuits being flexible such that they are capable of conforming to the surface contours of an object as a surface of the apparatus is pressed against it and an adaptive backing positioned behind the transmitter and receiver circuits in the scanning apparatus and configured to, as the scanning apparatus is pressed against the object, conform to the flexible circuits.

The scanning apparatus may comprise a dry coupling that is positioned in front of the transmitter and receiver circuit in the scanning apparatus.

The dry coupling may be configured to act as a transmission medium for conducting scanning signals into the object.

The dry coupling may form the surface of the scanning module.

The dry coupling may be flexible such that, when the surface of the scanning module is pressed against an object to be scanned, the dry coupling adapts to the surface contours of the object.

The flexible circuits may be configured to adapt to the surface contours of the object by flexing in conformity with the dry coupling as it adapts to the surface contours of the object.

The flexible circuits may be configured to flex inwardly in conformity with any inward deflection of the dry coupling into the scanning apparatus.

The adaptive backing may be compressible.

The scanning apparatus may comprise a relatively rigid surface positioned behind the adaptive backing in the scanning apparatus, the adaptive backing being configured to adapt to the shape of the flexible circuits by compressing against the rigid surface to accommodate any flexing of the flexible circuits.

The rigid frame may be configured to hold the scanning module such that the flexible circuits are sandwiched between the dry coupling and the adaptive backing.

The rear of the solid frame may form the solid surface against which the adaptive backing is compressed.

The front of the solid frame may be open such that the dry coupling forms the surface of the scanning module.

The transmitter circuit and the receiver circuit may be respectively configured to transmit and receive ultrasound signals.

The transmitter and receiver circuits may be configured to act as an ultrasound transducer.

The scanning apparatus may be configured to scan the object by transmitting ultrasound signals at the object and receiving reflections of those ultrasound signals from the object, the adaptive backing being configured to absorb substantially all of the reflected signals that reach it.

The thickness of the adaptive backing may be dependent on a compressibility of a material from which it is formed.

The dry coupling may be less compressible than the adaptive backing.

According to a second embodiment, there is provided a scanning apparatus for scanning a sample to a particular depth, comprising, a transmitter unit configured to transmit a scanning pulse at the sample, a receiver unit configured to receive reflections of the scanning pulse from the sample, a detection unit configured to detect reflections that have traveled from the particular depth in the sample to the scanning apparatus and a dry coupling that acts as a transmission medium to conduct the scanning pulse into the sample, the dry coupling being sufficiently thick for a reflection that has traveled from the particular depth to arrive at the scanning apparatus before a reflection that represents a second reflection of the scanning pulse off the boundary between the dry coupling and the sample.

The detection unit may be configured to time gate the received reflections so that the reflection that has traveled from the particular depth is detected and the reflection that represents the second reflection is not detected.

The dry coupling may be between 1 mm and 10 mm thick. The dry coupling may be between 1 mm and 5 mm thick.

According to a third embodiment, there is provided a method of manufacturing a scanning apparatus comprising designing the apparatus, including: determining a particular depth in a sample that the scanning apparatus is to be capable of scanning to; and selecting a thickness for a dry coupling to be used to conduct scanning pulses into the sample in dependence on the particular depth; and materially producing the apparatus so designed.

The method of manufacturing may include selecting the thickness for the dry coupling to be sufficient for a reflection that has traveled from the particular depth in the sample to arrive at the scanning apparatus before a reflection that represents a second reflection of the scanning pulse off the boundary between the dry coupling and the sample.

The method of manufacturing may include designing a detection unit so that it can be configured to detect a reflection that has traveled from the particular depth and not detect the reflection that represents the second reflection of the scanning pulse off the boundary between the dry coupling and the sample.

The method of manufacturing may include designing the detection unit to comprise a time gate.

DESCRIPTION OF DRAWINGS

The present invention will now be described by way of example with reference to the accompanying drawings. In the drawings.

DETAILED DESCRIPTION

A scanning apparatus may be provided with an adaptive backing to help its scanning surface conform to non-flat, uneven surfaces. The apparatus suitably comprises a scanning module comprising a receiver circuit and a transmitter circuit. The scanning module may be configured to transmit and receive ultrasound pulses via the transmitter and receiver circuits, although any suitable scanning signals might be used. Both circuits are flexible so that they can adapt to the surface contours of an object. The adaptive backing is positioned behind the transmitter and receiver circuits. It is configured to conform to the shape of the circuits as they flex in response to being pressed against a non-flat surface.

Figure 1:
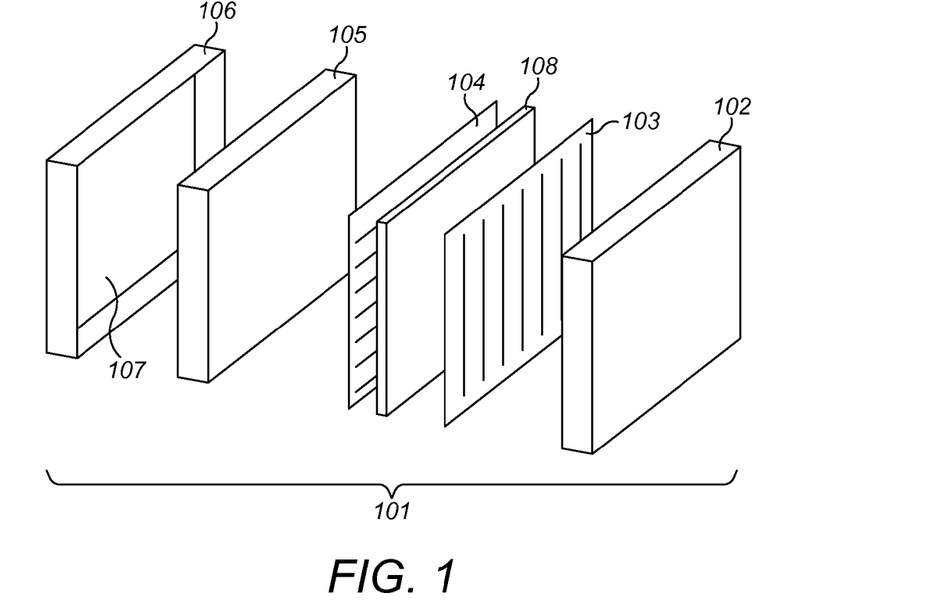
FIG. 1 shows an example of the layers comprised in a scanning apparatus.

An example of a scanning apparatus is shown in FIG. 1. The apparatus has been deconstructed into its component parts for ease of illustration. The apparatus is shown generally at 101. The apparatus comprises a dry coupling 102. The dry coupling forms the scanning surface. It is configured to act as a transmission medium for the scanning signals. In one example the scanning signals are ultrasound signals, which tend to be attenuated strongly by air. It is important that the dry coupling be capable of conforming to any unevenness in the surface of the sample so that the ultrasound does not encounter air on its path into the sample. Suitably the dry coupling is both flexible and soft. Preferably the dry coupling is compressible so that it deforms inwardly into the apparatus as the operator presses the scanning surface against the sample.

The receiver and transmitter circuits 103, 104 are positioned behind the dry coupling. They may be formed from very thin printed circuited boards. In one example the transmitter and receiver circuits comprise a plurality of elongated electrodes deposited in parallel lines on a flexible base layer. The transmitter and receiver circuits may be laminated together. They may be arranged so that their respective electrodes overlap at right angles to form an intersecting pattern. The intersections form an array of scanning elements. The transmitter and receiver circuits may sandwich a layer of acoustic material 108 to form an ultrasound transducer.

The transmitter and receiver circuits are flexible so they are capable of flexing or deflecting in conformity with any movement of the dry coupling. If the dry coupling is pressed inwards so that it intrudes on the space normally occupied by the flexible circuits, the flexible circuits will flex inwardly to accommodate it.

An adaptive backing 105 is positioned behind the transmitter and receiver circuits. It is conformable to the flexible transmitter and receiver circuits. Suitably the dry coupling is compressible. In a preferred example the adaptive backing is less compressible than the dry coupling, so that the dry coupling is not capable of adopting a curvature that cannot be matched by the other layers of the apparatus. The adaptive backing might be softer than the dry coupling.

The dry coupling, flexible circuits and adaptive backing are held in place by a frame 106 that is relatively rigid compared to the other layers. It forms a firm surface 107 behind the adaptive backing. Effectively the adaptive backing gives the transmitter and receiver circuits the ability to flex inwardly as the apparatus is pressed against a non-flat surface and protects them from being damaged against the rigid frame as they do so.

The apparatus is thus capable of adapting to non-flat surfaces. It is particularly suitable for applications in which sample surfaces may be curved or uneven. An example is non-destructive testing. It is also particularly helpful when the apparatus uses (i) a matrix array for transmitting and receiving scanning signal and (ii) a dry coupling for conducting scanning signals into the sample.

An advantage of having a matrix array is that it is two dimensional, so a three-dimensional section of the sample can be scanned while the apparatus is held stationary against the sample surface. Some other scanners have only a single line of scanning elements. The scanner then has to be moved across the sample's surface in order to scan a two-dimensional section. This is disadvantageous but it does mean that the apparatus is naturally adaptable to curved surfaces. The examples described herein enable an apparatus comprising a matrix array to conform to a non-flat sample surface. The advantages of stationary scanning and scanning curved surfaces can therefore be combined in a single apparatus.

Using a dry coupling is advantageous in non-destructive testing applications because it avoids having to use a liquid coupling or gel. A dry coupling is, however, not necessarily as adaptable to uneven sample surfaces as a liquid. Having a flexible dry coupling is helpful but there is a risk that other components in the apparatus, particularly the transmitter and receiver circuits that are necessarily positioned behind the dry coupling to generate the scanning signals, may get damaged if the dry coupling deflects a relatively large amount to accommodate a curved sample. Using a combination of flexible circuits with an adaptive backing allows the apparatus to deal effectively with curved surfaces.

Figure 2:
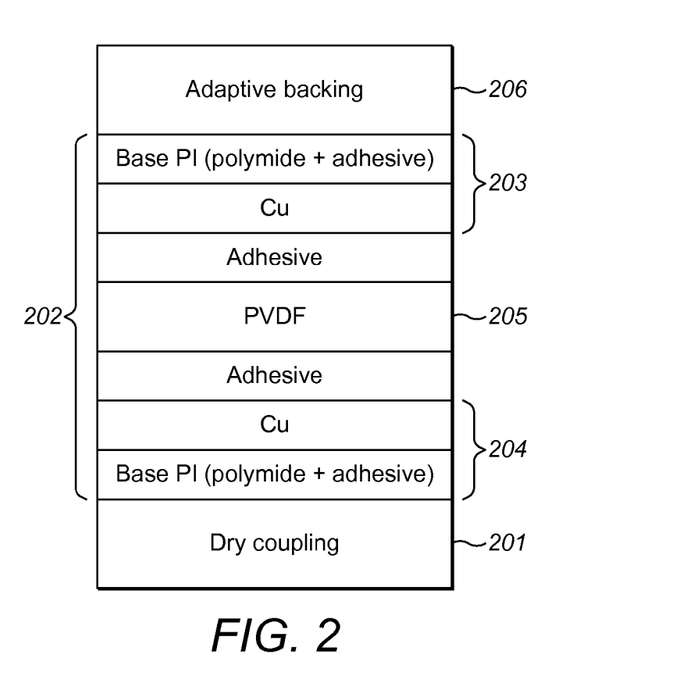
FIG. 2 shows an example of the layers comprised in a scanning apparatus.

An example of the layers that may be comprised in a scanning apparatus are shown in FIG. 2. The dry coupling 201 may be formed of an elastomer or any other suitable material. The thickness of the dry coupling may be adapted to the thickness of the sample to be scanned. (This is described in more detail below.) Behind the dry coupling is a transducer laminate 202. It is comprised of transmitter 203 and receiver 204 circuits that are respectively formed of copper deposited on a polyimide film. Each copper layer may form a series of electrodes. The electrodes might also be formed of other materials—gold, for example. A layer of piezoelectric material 205 (PVDF in this example) is sandwiched between the copper layers. This layer generates ultrasound signals when a high-voltage pulse train is sent out on the transmitter electrode, causing the piezoelectric layer to start vibrating and output an ultrasonic wave. In other examples the transducer might not comprise the adhesive or base film layers. The electrodes might be deposited directly on the piezoelectric layer.

The number of transmitter and receiver electrodes is scalable. Hence transducers can be designed of any desired size and shape. The electrode width is also scalable to adjust the amount of energy output per electrode. The electrode width can also be adjusted in dependence on the desired focus. The distance between the electrodes might also be varied. Generally it is preferred to have small gaps between neighbouring electrodes to maximise ultrasound energy by stimulating as large an area of the piezoelectric layer as possible. The thickness of the electrodes may be chosen to control factors such as frequency, energy and beam focus. The thickness of the base film may be chosen to control factors such as signal shape, frequency and energy. The PVDF thickness can also be adapted to change signal shape, frequency and energy (which are also dependent on the transmitting pulse shape). The dry coupling thickness can be adapted to create a particular time lag between transmitting the ultrasound pulses and receiving reflections of them from the sample.

The adaptive backing 206 should be thick enough to provide good adaptation to curved/uneven surfaces. The thickness also depends on the flexibility of the material from which the adaptive backing is formed. In many embodiments the adaptive backing will adapt to the curvature of the flexible circuits and dry coupling in front of it by compressing against the relatively rigid surface provided by the frame. The adaptive backing is preferably thick enough to absorb any ultrasound reflections that penetrate through the transmitter/receiver circuits. The relatively rigid surface behind the adaptive backing layer reflects ultrasound waves; therefore, it is important that the ultrasound signal has died out sufficiently before reaching it. The adaptive backing is thus preferably formed from a material with good damping of ultrasound signals. The thickness is thus also dependent on the damping properties of the material from which the adaptive backing is formed. In a different arrangement it might be possible to form the adaptive backing from a material that shows good reflection of ultrasound, so that reflection from the adaptive backing forms part of the transmitted pulse.

The adaptive backing is suitably between 1 mm and 10 mm thick. In one example the thickness is around 3 mm and the adaptive backing is formed of a silicone (e.g. EL RT 743LV-K). This is an example only as there is a wide range of materials (including many silicones) that would be suitable for the adaptive backing.

In most embodiments the apparatus will have a scanning surface that is substantially flat when the apparatus is not in use. Usually this means that the surface of the dry coupling exterior to the apparatus is flat, which in turn will usually mean that the transmitter and receiver circuits are flat and similarly for the surface of the adaptive backing that contacts the transmitter and receiver circuits. The transmitter and receiver circuits could be designed to have any desired shape, however, including convex or concave designs. The exterior surface of the dry coupling might also be formed to have a convex or concave shape. The apparatus might thereby be adapted to scan samples having particularly pronounced curvature. The interior surface of the dry coupling might mirror the concave/convex shape of its exterior surface or might be substantially flat. In practice a dry coupling of uniform thickness is likely to be preferred, particularly in non-destructive testing applications where accurate depth measurement is important. This will require matching curvature in the transmitter/receiver circuits and adaptive backing.

For ease of use the dry coupling is preferably sufficiently flexible and/or compressible to conform to an uneven or curved sample surface on being pressed against the surface by a human operator using a relatively low degree of force. The rigid frame is only "rigid" relative to the flexibility of the other layers, namely the adaptive backing, transmitter/receiver circuits and dry coupling. Preferably the rigid frame does not deform or flex on being pressed against the sample surface with a degree of force that is sufficient to adapt the other layers to the sample surface. The rigid frame may be made of rubber.

In one example the thickness of the dry coupling may be adapted to a particular scanning depth. The scanning depth may be the thickness of the sample if is desired to scan all of the sample. The scanning depth could be less than the thickness of the sample if only a particular section of the sample is to be scanned.

The thickness of the dry coupling may be selected during the manufacturing process as part of designing the scanning apparatus for a particular application. The thickness of the dry coupling affects the delay that the apparatus sees between transmitting scanning pulses at the sample and receiving reflections of them. The apparatus is suitably configured to transmit scanning pulses having a particular shape so that it can recognise reflections of those pulses and determine how long those reflections took to travel through the sample back to the apparatus. Reflections are normally triggered by impedance mismatches between materials that the scanning pulses encounter at the boundary between one material/substance and another. The time the reflections take to travel back to the apparatus allows it to work out how deep the material boundary that triggered the reflection is in the sample. The apparatus suitably includes a detection unit (which may be at least partly implemented by a signal processor) for recognising reflections of the transmitted pulses.

Figure 3:
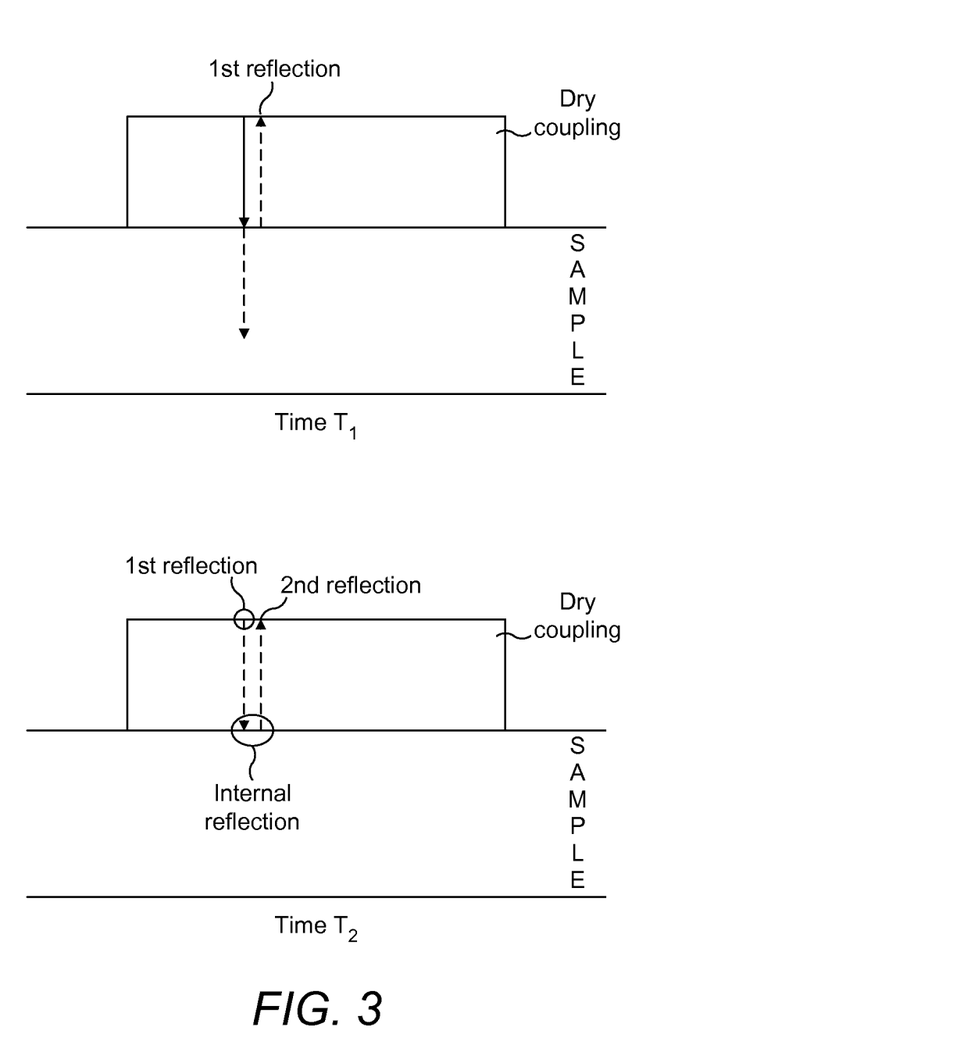
FIG. 3 shows an example of a scanning pulse being internally reflected by a dry coupling.

The dry coupling acts as a transmission medium for coupling the scanning signals into the sample. The dry coupling is preferably formed of a material that propagates the scanning signals well. There will inevitably be some impedance mismatch between the dry coupling and the sample, however, which will trigger a reflection of the scanning pulse. This reflection is generally not of interest. The apparatus can effectively ignore it by time gating the received signal. At least part of the first reflection may itself be reflected by the boundary between the dry coupling and the transmitter/receiver circuits, however, leading to internal reflection of the scanning pulse within the dry coupling. This is illustrated in FIG. 3: the first reflection is triggered by the boundary between the outer surface of the dry coupling and the sample; this reflection is then internally reflected by the inner surface of the dry coupling to form the second reflection of the scanning pulse off the dry coupling-sample boundary to be received at the apparatus. This second reflection is also not of interest; in fact, it is actually problematic as it could be interpreted as representing a structural feature within the sample.

In pre-existing scanning systems this second reflection off the dry coupling is generally not a concern. It can be straightforwardly dealt with by time gating the received signal so that the detection unit does not look for reflections in the part of the signal that contains the second reflection. This is only possible, however, when the scanning apparatus is only used to look at relatively shallow depths in the sample (e.g. for reading matrix codes that are covered by paint). For an apparatus that is configured to scan a sample at depth, the second dry coupling reflection cannot be removed by time gating without also losing reflections of interest.

The dry coupling is suitably thick enough so that the second dry coupling reflection is received after any reflections that would be received from the deepest point of interest in the sample. In many applications this will be the "back wall" of the sample. The appropriate dry coupling thickness is therefore dependent on the scanning depth. It is also dependent on the relative speed at which the scanning pulses travel in the dry coupling and the sample.

The dry coupling is suitably more than 0.5 mm thick and is preferably at least 1 mm thick. Preferably the dry coupling is between 1 mm and 10 mm thick, and more preferably it is between 1.5 mm and 5 mm thick. The scanning depth is preferably between 0 and 20 mm and most preferably between 0 and 15 mm. The dry coupling is suitably thick enough for greatest depth the apparatus is capable of scanning to. This may be determined by the time gates and/or other settings in the apparatus. Note that the configuration of the apparatus may be altered during use, e.g. by the operator adjusting the time gates. Typically the operator will not be able to override a maximum depth that the apparatus is capable of scanning to, however.

One way of dealing with the second reflection would be to make the dry coupling thicker than any conceivable sample. The ultrasound wave spreads more and loses energy the longer they travel, however, so the dry coupling pad is preferably no thicker than needed to delay the second reflection.

In one embodiment, dry couplings of varying thicknesses could be provided with the scanning apparatus. The operator could then affix the dry coupling that was most appropriate for the required scanning depth. One way of doing this might be to have a scanning module comprising the dry coupling, the transmitter and receiver circuits and the adaptive backing that the operator could affix to the apparatus as required. This would increase costs, however, so it might be preferable approach to select the appropriate dry coupling thickness during the design and manufacture process.

Figure 4:
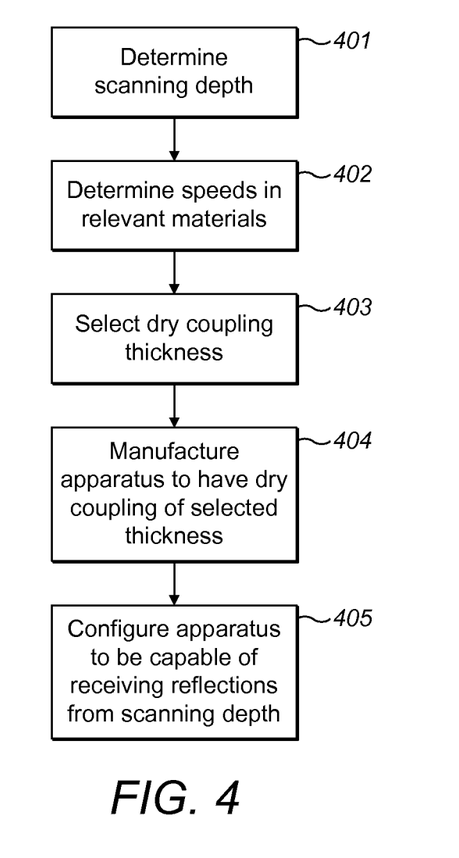
FIG. 4 shows an example of a method of manufacture.

An example of a design and manufacture process is shown in FIG. 4. The process starts in step 401 with the determination of the required scanning depth. Step 402 is an optional step of determining the speed at which the scanning pulses will travel in the dry coupling and the material of the expected sample. In practice it is likely that this step will have been performed previously to develop a tool such as a look-up table for translating a required scanning depth into a corresponding dry coupling thickness. In step 403 the appropriate dry coupling thickness is selected. The apparatus is manufactured in step 404 to include the dry coupling of the selected thickness. In step 405 the apparatus is configured to be capable of detecting reflections from the scanning depth. This is shown as a separate step in FIG. 4 for ease of illustration. In practice step 405 may be performed as part of step 404.

Figure 5:
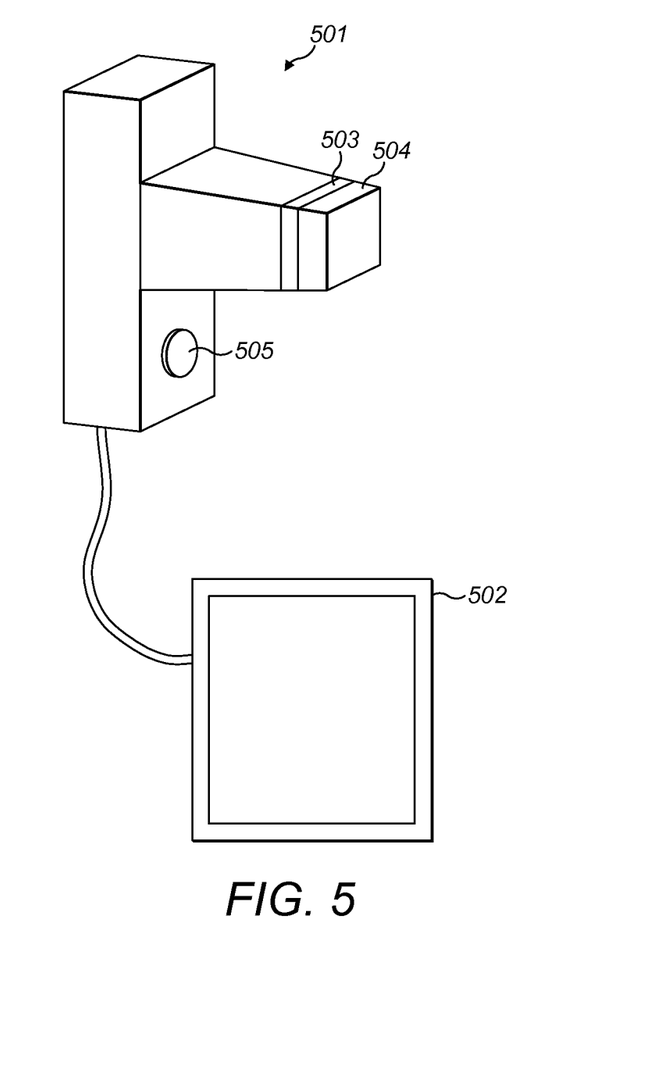
FIG. 5 shows an example of a scanning apparatus.

An example of a handheld device for imaging below the surface of an object is shown in FIG. 5. The device 501 could have an integrated display, but in this example it outputs images to a tablet 502. The device could also output to any suitable display, including a PC, laptop, pda etc. The connection with a separate could be wired, as shown, or wireless. The device has a matrix array 503 for transmitting and receiving ultrasound signals. Suitably the array is implemented by an ultrasound transducer comprising a plurality of electrodes arranged in an intersecting pattern to form an array of transducer elements. The transducer elements may be switched between transmitting and receiving. The handheld apparatus comprises a dry coupling layer 504 for coupling ultrasound signals into the object. The dry coupling layer also delays the ultrasound signals to allow time for the transducers to switch from transmitting to receiving. A dry coupling layer offers a number of advantages over other imaging systems, which tend to use liquids for coupling the ultrasound signals. This can be impractical in an industrial environment.

If the liquid coupler is contained in a bladder, as is sometimes used, this makes it difficult to obtain accurate depth measurements which is not ideal for non-destructive testing applications.

The matrix array 503 is two dimensional so there is no need to move it across the object to obtain an image. A typical matrix array might be 30 mm by 30 mm but the size and shape of the matrix array can be varied to suit the application. The device may be straightforwardly held against the object by the operator. Commonly the operator will already have a good idea of where the object might have sub-surface flaws or material defects; for example, a component may have suffered an impact or may comprise one or more drill or rivet holes that could cause stress concentrations. The device suitably processes the reflected pulses in real time so the operator can simply place the device on any area of interest.

The handheld device also comprises a dial 505 that the operator can use to change the pulse shape and corresponding match filter. The most appropriate pulse shape may depend on the type of structural feature being imaged and where it is located in the object. The operator views the object at different depths by adjusting the time-gating via the display. Having the apparatus output to a handheld display, such as tablet 502, or to an integrated display, is advantageous because the operator can readily move the transducer over the object, or change the settings of the apparatus, depending on what he is seeing on the display and get instantaneous results. In other arrangements, the operator might have to walk between a non-handheld display (such as a PC) and the object to keep rescanning it every time a new setting or location on the object is to be tested.

The apparatus and methods described herein are particularly suitable for detecting debonding and delamination in composite materials such as carbon-fibre-reinforced polymer (CFRP). This is important for aircraft maintenance. It can also be used detect flaking around rivet holes, which can act as a stress concentrator. The apparatus is particularly suitable for applications where it is desired to image a small area of a much larger component. The apparatus is lightweight, portable and easy to use. It can readily carried by hand by an operator to be placed where required on the object.

The expressions "behind", "in front of" and the like are used herein to denote relative positions of various components in the apparatus. In some embodiments a layer that is "behind" or "in front of" another may be positioned directly by that other layer in the apparatus so that the two are touching; in other embodiments there may be one or more intervening layers. The "front" of the apparatus is represented by the scanning surface. The inward direction points away from the scanning surface towards the interior of the apparatus.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A scanning apparatus comprising:
   a receiver circuit and a transmitter circuit, both circuits being flexible such that they are capable of conforming to the surface contours of an object as a surface of the apparatus is pressed against it; and
   an adaptive backing positioned behind the transmitter and receiver circuits in the scanning apparatus and configured to, as the scanning apparatus is pressed against the object, conform to the flexible circuits.

2. A scanning apparatus as claimed in claim 1, comprising a dry coupling that is positioned in front of the transmitter and receiver circuit in the scanning apparatus.

3. A scanning apparatus as claimed in claim 2, the dry coupling being configured to act as a transmission medium for conducting scanning signals into the object.

4. A scanning apparatus as claimed in claim 2, the dry coupling forming the surface of the scanning apparatus.

5. A scanning apparatus as claimed in claim 2, the dry coupling being flexible such that, when the surface of the scanning apparatus is pressed against an object to be scanned, the dry coupling adapts to the surface contours of the object.

6. A scanning apparatus as claimed in claim 2, the flexible circuits being configured to adapt to the surface contours of the object by flexing in conformity with the dry coupling as the dry coupling adapts to the surface contours of the object.

7. A scanning apparatus as claimed in claim 2, the flexible circuits being configured to flex inwardly in conformity with any inward deflection of the dry coupling into the scanning apparatus.

8. A scanning apparatus as claimed in claim 1, the adaptive backing being compressible.

9. A scanning apparatus as claimed in claim 1, comprising a relatively rigid surface positioned behind the adaptive backing in the scanning apparatus, the adaptive backing being configured to adapt to the shape of the flexible circuits by compressing against the rigid surface to accommodate any flexing of the flexible circuits.

10. A scanning apparatus as claimed in claim 2, the dry coupling being less compressible than the adaptive backing.

11. A scanning apparatus as claimed in claim 9, comprising a rigid frame configured to hold the flexible circuits between a dry coupling and the adaptive backing.

12. A scanning apparatus as claimed in claim 11, the rear of the rigid frame forming the rigid surface against which the adaptive backing is compressed.

13. A scanning apparatus as claimed in claim 11, the front of the rigid frame being open such that the dry coupling forms the surface of the scanning apparatus.

14. A scanning apparatus as claimed in claim 1, the transmitter circuit and the receiver circuit being respectively configured to transmit and receive ultrasound signals.

15. A scanning apparatus as claimed in claim 1, the transmitter and receiver circuits being configured to act as an ultrasound transducer.

16. A scanning apparatus as claimed in claim 1, the scanning apparatus being configured to scan the object by transmitting ultrasound signals at the object and receiving reflections of those ultrasound signals from the object, the adaptive backing being configured to absorb substantially all of the reflected signals that reach it.

17. A scanning apparatus as claimed in claim 1, the receiver circuit and the transmitter circuit having a non-planar shape in a non-deformed state.

18. A method of scanning an object using a scanning apparatus, the scanning apparatus comprising a receiver circuit and a transmitter circuit, both circuits being flexible; and an adaptive backing positioned behind the transmitter and receiver circuits in the scanning apparatus, the method comprising:
   pressing a surface of the scanning apparatus against the object such that the receiver circuit and the transmitter circuit conform to surface contours of the object; and such that the adaptive backing conforms to the flexible circuits as the scanning apparatus is pressed against the object.

* * * * *